United States Patent [19]

Wheeldon et al.

[11] Patent Number: 4,604,034
[45] Date of Patent: Aug. 5, 1986

[54] PERISTALTIC PUMPS

[75] Inventors: Peter G. Wheeldon, Guildford; John Kent, Byeworth, Nr Petworth, both of England

[73] Assignee: Peritronic Medical Industries plc, London, England

[21] Appl. No.: 606,016

[22] Filed: May 2, 1984

[30] Foreign Application Priority Data

May 3, 1983 [GB] United Kingdom ............... 8312069

[51] Int. Cl.⁴ ...................... F04B 49/00; F04B 49/10; A61F 2/54
[52] U.S. Cl. ...................................... 417/18; 417/53; 417/63; 604/65; 604/67
[58] Field of Search ................... 604/65, 67; 128/DIG. 12; 417/18, 22, 53, 12, 63

[56] References Cited

U.S. PATENT DOCUMENTS

| | | | |
|---|---|---|---|
| 3,249,059 | 5/1966 | Renn | 417/477 |
| 3,335,670 | 8/1967 | Williams | 417/53 |
| 4,111,336 | 9/1978 | Ward | 222/63 |
| 4,299,541 | 11/1981 | Ohara | 417/12 |
| 4,326,837 | 4/1982 | Gilson | 417/12 |
| 4,373,525 | 2/1983 | Kobayaski | 128/DIG. 12 |
| 4,444,546 | 4/1984 | Pazemenas | 417/63 |
| 4,467,844 | 8/1984 | Gianfilippo | 604/65 |
| 4,468,219 | 8/1984 | George | 128/DIG. 12 |
| 4,474,309 | 10/1984 | Solomon | 417/22 |

FOREIGN PATENT DOCUMENTS 100682 2/1984 European Pat. Off. .

Primary Examiner—William L. Freeh
Attorney, Agent, or Firm—Biebel, French & Nauman

[57] ABSTRACT

Control apparatus for a stepping motor driving a peristaltic pump comprises a presettable downcounter for supplying drive pulses to the stepping motor at different repetition rates so as to regulate the speed of rotation of the motor, processing means for controlling the downcounter so that the motor is normally operated to drive the pump at a predetermined pumping rate, and a sensor for detecting indexing marks at spaced positions about the pump head, the processing means being responsive to the sensor detecting the index marks to alter the count in the downcounter so as to increase the motor speed for a predetermined number of motor steps upon detection of each index mark. After the predetermined number of steps at increased speed, the processing means resets the downcounter to its normal setting, so that the motor operates at the required pumping rate for a further predetermined number of motor steps and until detection of the next successive index mark of the head. Hence, the drive motor rotates or skips more rapidly during alternate periods corresponding to dwell periods of the peristaltic pump when reduced or no fluid flow would normally occur and, consequently, the pump delivers fluid at a more constant flow rate.

5 Claims, 2 Drawing Figures

PERISTALTIC PUMPS

BACKGROUND OF THE INVENTION

The present invention is concerned with improving the operating characteristics of peristaltic pumps, more particularly, by regulating the operation of the pump drive motor. Whilst it is specifically directed to improving the operation of peristaltic medical infusion pumps, is is equally applicable to other peristaltic pumps where volumetric accuracy and constancy or uniformity of flow are important requirements.

The peristaltic pumping action is well suited for use in a medical infusion pump because it is applied externally to the fluid delivery tube and, consequently, does not interfere with the sterile state which must be maintained for the infusion fluid within the tube. Furthermore, the pumping action can be applied at any point on the delivery tube of a simple I.V. set, thus avoiding the need for special and expensive I.V. sets of the cassette type, as used on many volumetric infusion pumps.

There are various types of peristaltic pump, but the simplest, most reliable and least expensive is that based on a rotary action in which a rotary pump head, including a plurality of rollers, is rotated to engage the rollers successively with a delivery tube to pump fluid along the tube. This type of rotary pump mechanism is well known.

A major problem which exists in rotary peristaltic pumps is that the resulting delivery of fluid occurs in a series of pulses or surges, the frequency of which is equal to the frequency of the passage of successive rollers in contact with the delivery tube. This flow pattern is inherent in conventional rotary peristaltic pumps. The effect is that fluid is delivered at a widely varying rate during a pump cycle and this can be unacceptable in infusion procedures in which uniformity of delivery rate is a requirement. Moreover, the continuous change in flow rate can cause instability in sensitive feed-back control systems which are designed to ensure that fluid is delivered at a constant rate.

One convenient device for driving the pump head of a rotary peristaltic pump is a stepping motor, since such a motor is capable of offering a wide range of rotational speeds using a simple, gearless direct drive transmission. Also, the digital system used to rotate the motor is well suited to the type of electronic motor speed control circuitry used with a feed-back loop system for maintaining accuracy of pumping performance.

For the purposes of monitoring the flow pattern of fluid delivered by a typical peristaltic pump, tests were carried out on a rotary peristaltic pump arrangement having a rotary pump head comprising five equally spaced rollers and driven by a stepping motor having 200 steps per revolution. From these tests, it was found that during the passage of each roller in contact with the delivery tube, constant flow was maintained through the tube for 26 steps of the motor, immediately followed by a sequence of 14 motor steps during which there was no flow at all in the downstream or positive direction. During this dwell period, there was often some evidence of negative flow. This means that, in normal operation, the pump is delivering no fluid for over one-third of its operating time and is delivering fluid at a rate 50% higher than the average rate for nearly two-thirds of the time.

SUMMARY OF THE INVENTION

It is an object of the present invention to alleviate the aforementioned problem experienced with existing peristaltic pumps and to provide for control of the pump drive motor so as to achieve a more constant flow rate throughout the cycle of operations of such a pump.

To this end, the invention provides control apparatus for the drive motor of a peristaltic pump, comprising regulating means for supplying an adjustable drive signal to the motor, processing means for controlling the regulating means, whereby the motor is operated to drive the pump at a predetermined pumping rate, and sensing means for detecting predetermined successive positions of the pump head, said processing means being responsive to the sensing means detecting each predetermined successive position of the pump head to adjust the regulating means so as to increase the motor speed for a predetermined period upon detection of each successive position, whereafter the processing means resets the regulating means to operate the motor at the predetermined pumping rate until detection of the next successive predetermined position of the head. Hence, with the invention the drive motor is arranged to rotate more rapidly during periods corresponding to the dwell periods, when no or reduced fluid flow would normally occur, and consequently the pump functions to deliver fluid at a more constant or uniform flow rate than hitherto.

The invention is particularly suitable for controlling the operation of a stepping motor drive of a peristaltic pump. In this application, the regulating means comprises a pulse counter for supplying drive pulses to the stepping motor at an adjustable pulse rate. The processing means controls the setting of the counter so that the speed of the motor normally corresponds to the predetermined pumping rate. It is arranged to be responsive to the sensing means detecting each predetermined successive position of the pump head and corresponding to the start of a flow dwell period so as to adjust the counter to increase the drive pulse rate, and thus, the motor speed, for a predetermined number of steps of the motor, whereafter the processing means resets the counter so as to rotate the motor at the predetermined pumping rate until detection of the next successive position. By arranging the stepping motor to index rapidly through a number of steps, which is equivalent to the dwell period, so that these steps are covered, for example, in a time approximately equivalent to one step during the period in which flow is normally maintained by the pump, the latter can be operated to deliver at a constant rate throughout its entire running cycle. This rapid indexing or "skipping" of the motor must occur at the beginning of the dwell period associated with the passage of each roller, and the sensing means achieves this.

The invention enables monitoring of the operation of the stepping motor and detection of when it is overloaded. or stalled. The stepping motor is arranged to operate in a succession of alternate run and skip sequences, each of which occurs over a predetermined number of steps of the motor. Hence, there are a discrete number of motor steps between each successive position of the pump head detected by the sensing means and, if the motor is operating in synchronism with its drive pulses, this can be detected by sensing coincidence between signals produced by the sensing means and upon delivery of a number of drive pulses corresponding to the discrete number of motor steps between successive sensed positions of the pump head. If such coincidence does not occur, then the pump is overloaded or stalled and an alarm condition can be called.

The invention may be incorporated in flow control apparatus, as described in our prior patent application EP-A-0100682, for a fluid dispensing system in which fluid is dispensed from a fluid container under the control of a rotary peristaltic pump. In such apparatus, the processing means is also arranged to be responsive to selection means for selecting a required flow rate and a weight sensing device for monitoring the weight loss of the fluid container as fluid is dispensed therefrom. It compares the selected flow rate with actual flow rate data derived from weight loss signals supplied by the weight sensing device and controls the regulating means so as also to adjust the speed of the pump motor in such a manner that the actual flow rate approaches or corresponds to the selected rate.

BRIEF DESCRIPTION OF THE DRAWINGS

In order that the present invention may be more readily understood, reference will now be made to the accompanying drawings, in which.

DESCRIPTION OF THE PREFERRED EMBODIMENT

Figure 1:
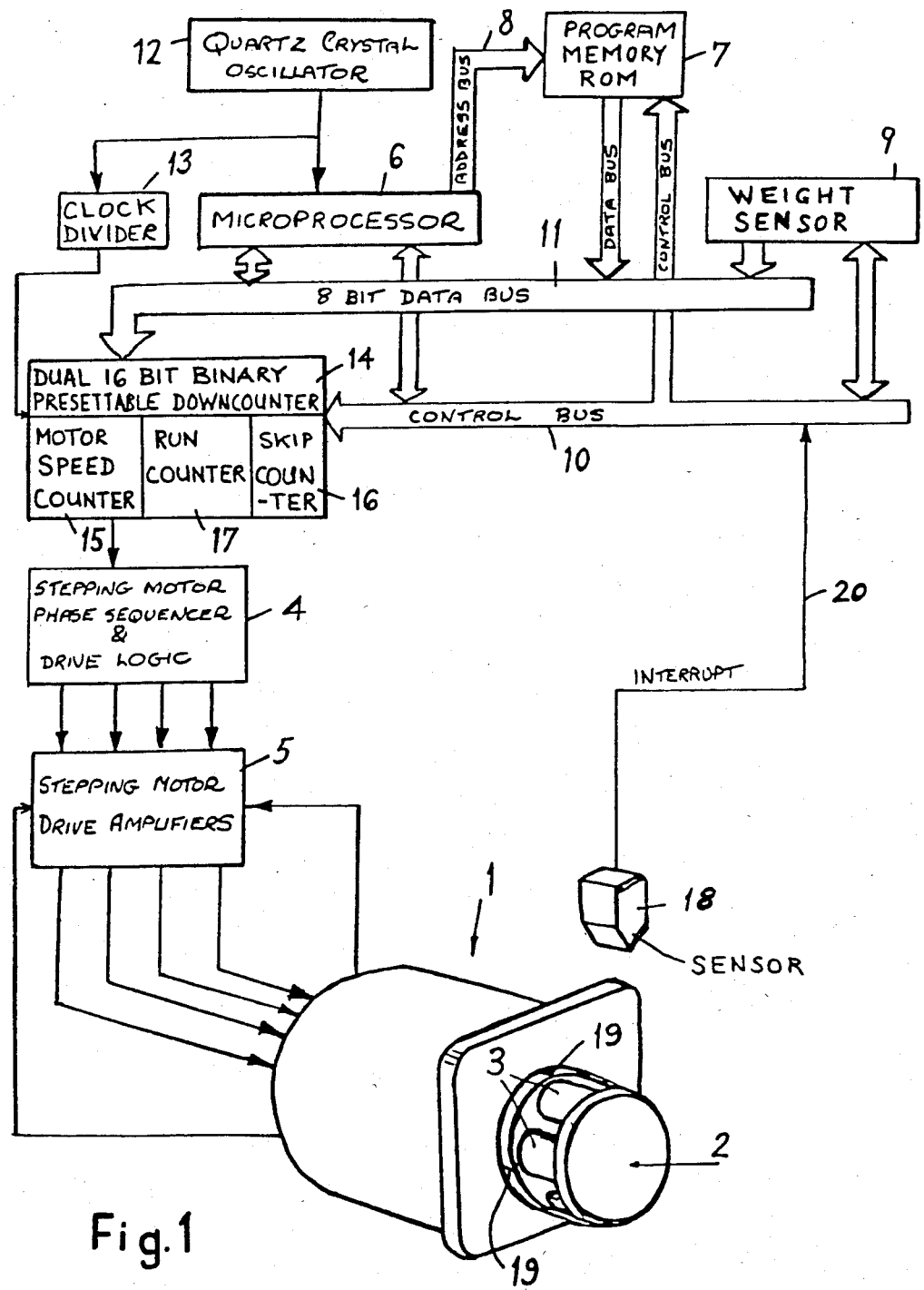
FIG. 1 is a schematic diagram illustrating the drive logic and control circuitry of a rotary peristaltic pump embodying the invention.

Referring to FIG. 1 of the drawings, 1 schematically illustrates a stepping motor connected to drive the pump head 2 of a rotary peristaltic pump. This pump head includes several rollers 3, arranged to be rotated successively into engagement with a delivery tube which is urged into engagement with the pump head by a tube holder (not shown) so that fluid is pumped along the delivery tube by a peristaltic action upon rotation of the head. For example, the rotary peristaltic pump may comprise five rollers 3 mounted in the rotary pump head 2 at equally spaced positions thereabout and freely rotatable about axes parallel to the axis of the rotary head. The rollers cooperate with an arcuate tube holder which is concentric with the head and which presses the delivery tube into contact with the rollers, as they move along a part of their circular path of travel, over an arc somewhat greater than the distance between two adjacent rollers. As the head rotates, the rollers successively and repeatedly engage the delivery tube urged towards the head by the tube holder so as to apply a peristaltic action to the delivery tube and pump the fluid through the tube in a succession of peristaltic cycles. The stepping motor 1 connected to rotate the pump head may, for example, be a four-phase motor having a 1.8° step that is, 200 steps per revolution. Trains of drive pulses are supplied to the motor via a conventional phase sequencer and drive logic circuit 4 and drive amplifiers 5.

With a rotary pump head having five equally spaced rollers, during each pumping pulse, the corresponding roller travels over an arc of contact with a delivery tube of 72° (360°/5). Having regard to the test results referred to above, this means that each roller initially produces flow through the delivery tube for only 47° of this arc (that is 26/26+14×72°) whilst the dwell portion of the cycle occurs over the remaining 25°. Because there are five rollers, this dwell period occurs at regular intervals and five times for each revolution of the pump head.

The principles of construction of a peristaltic pump are well known to persons skilled in the art and will not be described in more detail as they do not, themselves, form part of the present invention which is concerned with the control of such pumps. Hence, the structure particularly described above is only referred to for the purposes of explaining the pulsed delivery characteristic of a peristaltic pump, which it is the aim of the present invention to alleviate, and to illustrate how the frequency and duration of the dwell periods associated with peristaltic pumps may be deduced.

The control circuitry for the stepping motor comprises a central processing unit 6, conveniently, a microprocessor, such as, the 8-bit microprocessor marketed by RCA Inc. under the Model No. CDP 1806 Ace, having a program memory 7 (Read Only Memory or ROM) accessed via an address bus 8. A weight sensor 9 monitors the weight of a fluid container (not shown) from which fluid is dispensed under the control of the pump and produces weight signals corresponding to the loss in weight of the container as fluid is dispensed. These weight signals are processed by the microprocessor 6 which produces therefrom data identifying the actual flow rate. The microprocessor 6, program memory 7 and the weight sensor 9 are interconnected by control and data buses 10,11 and the arrangement of these components may be similar to the electronic flow control circuitry of the system described in our aforementioned EP-A-0100682.

A train of timing pulses is supplied by a quartz crystal oscillator 12 which is connected to the microprocessor 6 and, via a clock divider 13 feeding pulses at a constant rate, to a dual 16-bit binary presettable downcounter 14. One 16-bit counter 15 of this downcounter is connected to supply drive pulses to the phase sequencer and drive logic 4 of the stepping motor, whilst the other is separated into two 8-bit downcounters 16,17 respectively controlling the numbers of steps of the stepping motor to be operated at skip and normal running speeds. The counter 15 serves as a variable pulse divider for producing motor drive pulse trains at different repetition rates for regulating the speed of rotation of the stepping motor. The counters 15,16,17 are controlled by the microprocessor to which they are connected by the control and data buses 10,11.

Associated with the rotary pump head 2 is a photo sensor 18 for detecting the rotational position of the head. It senses several indexing marks 19 which are equally spaced about the pump head in predetermined positions with respect to the rollers 3 and corresponding to the start of a skip period for each roller. In response to sensing a mark 19, the sensor 18 supplies an interrupt signal to the microprocessor via the line 20 and the control bus 10.

Figure 2:
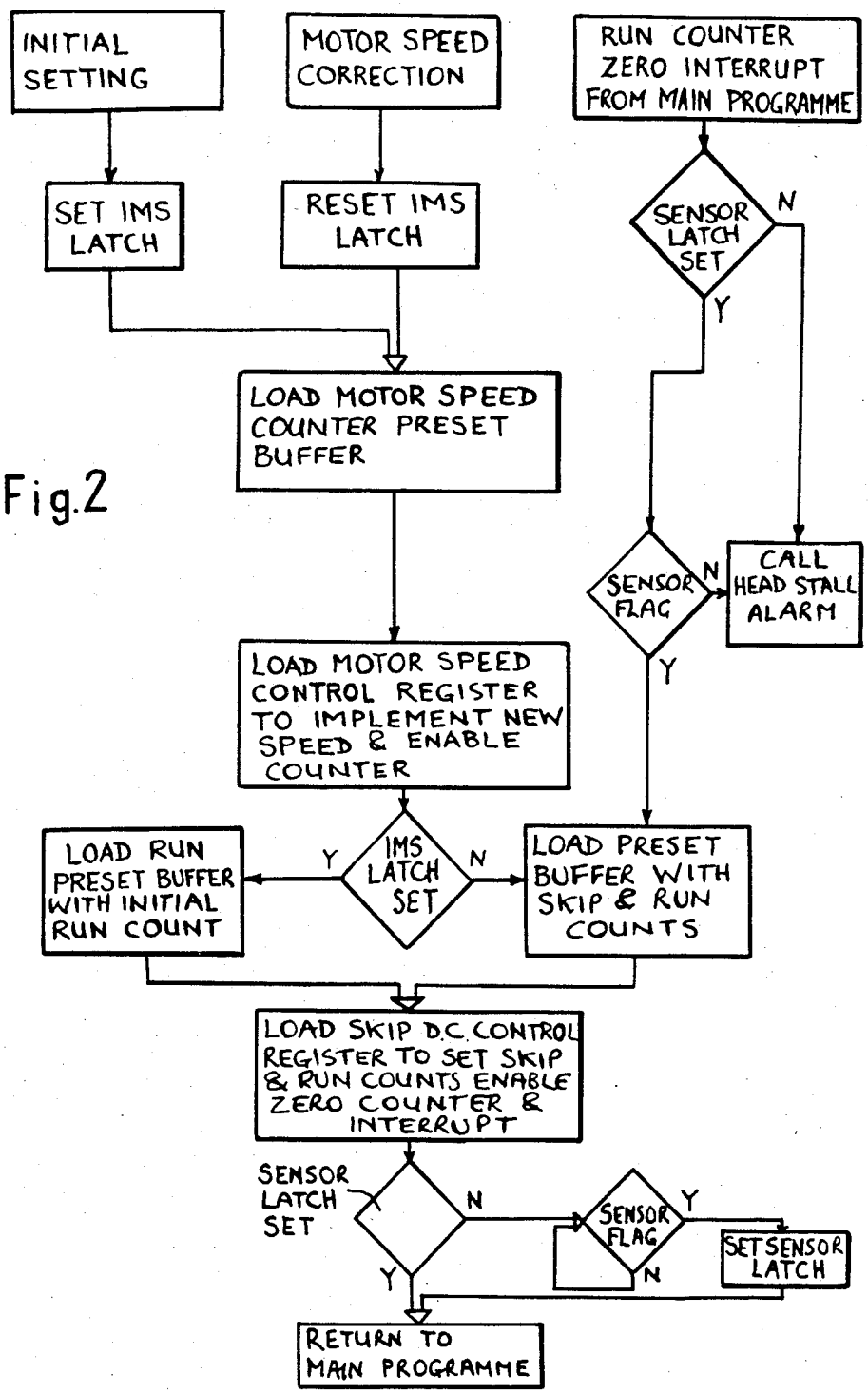
FIG. 2 is a flowchart illustrating the logical steps and operations executed by the CPU in producing skip operation of the stepping motor.

The operation of the pump will now be described and in this connection reference should also be made to the flowchart illustrated in FIG. 2. A desired pumping rate is first selected and data identifying the selected rate is loaded into the microprocessor 6. The latter stores this data and determines the initial speed at which the stepping motor 1 should rotate, in order nominally to deliver the selected flow rate by reference to the program memory 7. Upon fetching of the initial motor setting a speed from the program memory an initial motor speed latch (IMS latch) is set and the microprocessor loads this motor speed information onto the data bus 11 for presetting the buffer register of the motor speed counter 15 preparatory to loading the speed counter control register at the next step to implement the required speed and enable the counter. Hence, upon commencement of pumping, the counter 15 supplies a train of pulses to the phase sequencer and drive logic 4 at the required pulse rate to drive the motor 1 at a speed nominally corresponding to the selected pumping rate.

Whilst pumping proceeds, the microprocessor 6 also receives data from the weight sensor 9 and processes this to produce data identifying the actual flow rate. It sequentially compares this data with the selected rate data and accesses the program memory 7 so that data is supplied to the counter 15 to adjust the motor speed in such a manner that the actual pumping rate approaches the selected pumping rate. When a motor speed correction is required, the IMS latch is reset and the new motor speed data is preset into the buffer register of the counter 15 preparatory to loading into the control register of this counter at the next increment similarly to the initial motor speed setting.

Upon starting of the motor 1, the microprocessor 6 interrogates the IMS latch and, detecting this to be set, loads solely into the buffer register of the run counter 17 a count corresponding to the number of steps at which the motor is to be operated at normal running speed. This count is then loaded into the control register of the run counter and enables the latter. As the motor rotates, the run counter is downcounted by motor drive pulses from the counter 15 and, since the number of run steps of the motor exceeds the skip steps, assuming normal operation, the sensor 18 will detect a mark 19 on the head during this downcount, and an interrupt signal will be produced on the line 20 to set a sensor 18 latch. Each time the sensor detects a mark 19 the interrupt signal also sets a sensor 18 flag. Upon starting of the motor, the microprocessor repeatedly interrogates the sensor flag until it detects that this is set, whereupon the sensor latch is set and control returns to the main program. when the sensor latch is set, a run counter zero interrupt signal is supplied by the main program of the microprocessor which signals the microprocessor to load the buffer registers of both the skip and run counters 16,17 with the predetermined skip and run counts preparatory to loading into the control registers of those counters. If the sensor latch or flag has not been set, upon the occurrence of the zero interrupt signal from the main program, or the zero interrupt signal produced by the run counter 17, itself, upon being downcounted to zero, this indicates that the pump is overloaded or stalled and the program calls a pump stall alarm. Assuming there is no such fault, the skip and run counters 16,17 control the operation of the motor speed counter 15 so as to drive the motor alternately at the different speed normal run and skip rates. At the end of each normal run count, the run counter 17 produces the abovementioned zero interrupt signal and providing this is in synchronism with the interrupt signal produced by the sensor 18 upon sensing a mark 19 on the head, the motor is operating properly. If it does not, then the program calls into operation the head stall alarm and stops the motor. If the microprocessor 6 makes a motor speed correction during operation of the pump, upon detecting the IMS latch to be reset, it merely maintains the buffer registers of the skip and run counters 16,17 loaded with the predetermined skip and run counts.

When the sensor 18 detects a mark 19 on the pump head and, by this means detects the position at which a skip sequence should commence, the interrupt signal produced by the sensor 18 signals the microprocessor to reset the count in the motor speed counter 15 to the required value for the higher skip rate and motor drive pulses are supplied at this rate for the number of motor steps determined by the skip counter 16. Since it is desirable to complete the skip sequence in the minimum possible time the step rate during this sequence is fixed at the fastest rate at which the motor operates, that is, of the order of 500 steps per second. After the predetermined number of motor steps controlled by the skip counter 16, the microprocessor resets the register of the motor speed counter 15 to the normal running value determined to be required to achieve the selected flow rate, and the motor 1 is then driven at this slower running rate for the number of steps determined by the run counter 17 and until the next interrupt signal is produced by the sensor 18 and the microprocessor checks that this is synchronised with the zero interrupt signal produced on zeroising of the run counter 17, whereupon the sequences of operations is repeated.

Whilst a particular embodiment has been described, it will be appreciated that modifications can be made without departing from the scope of the invention as defined by the appended claims.

We claim:

1. In a peristaltic pump which is adapted to apply a peristaltic action in a succession of peristaltic cycles to a delivery tube disposed in said pump for pumping a fluid flow through said delivery tube, and which includes rotary means arranged to be driven by stepping motor means, the improvement consisting in control apparatus adapted to reduce the dwell period in each said peristaltic cycle, during which dwell period reduced fluid flow would normally occur, thereby to achieve more uniform flow of said fluid being pumped, said control apparatus comprising:

(a) means for producing electrical timing pulses,
(b) adjustable speed pulse counting means responsive to said timing pulses and connected to provide drive pulses for said stepping motor means in response to counting predetermined trains of said timing pulses,
(c) processing means for controlling said speed pulse counting means, whereby said stepping motor means is operated at a speed which drives said pump at a predetermined pumping rate,
(d) indexing means associated with said rotary means and defining a predetermined position of said rotary means, and
(e) sensing means for detecting said indexing means,
(f) said processing means being responsive to said sensing means detecting said indexing means to adjust said speed pulse counting means to increase the speed of said stepping motor means for a predetermined skip period after which skip period said processing means is adapted to reset said speed pulse counting means to operate said stepping motor means at said speed corresponding to said predetermined pumping rate until next detection of said indexing means, whereby said processing means is adapted to regulate said speed pulse counting means alternately to provide drive pulses at repetition rates corresponding to said predetermined pumping rate and said increased skip rate.

2. The peristaltic pump claimed in claim 1, including run pulse counting means and skip pulse counting means for controlling the number of steps at which said stepping motor is operated at said alternate pumping and skip rates, said run and skip counting means being controlled by said processing means and being responsive to said drive pulses provided by said speed pulse counting means.

3. The peristaltic pump claimed in claim 2, wherein said run and skip counting means are adapted to be set upon said sensing means detecting said indexing means and to produce a signal upon completion of each skip and run cycle, said processing means detecting synchronisation between said signal and a signal produced by said sensing means detecting said indexing means to monitor correct operation of said stepping motor.

4. In a method of operating a peristaltic pump which pumps fluid through a delivery tube disposed in said pump by applying a peristaltic action to said delivery tube in a succession of peristaltic cycles, and which includes rotary means arranged to be driven by stepping motor means, the improvement which consists in controlling the operation of said stepping motor means so as to reduce the dwell period in each said peristaltic cycle, during which dwell period reduced fluid flow would normally occur, thereby to achieve more uniform flow of said fluid being pumped, and which comprises the steps of:

(a) producing electrical timing pulses, (b) counting said timing pulses and producing drive pulses for said stepping motor means in response to counting predetermined trains of said timing pulses, (c) providing for the control of the repetition rate of said drive pulses by adjustment of the count of timing pulses required to produce each said drive pulse, (d) adjusting said count of said timing pulses to cause said stepping motor means to operate at a speed which drives said pump at a predetermined pumping rate, (e) detecting indexing means associated with said rotary means and defining a predetermined position of said rotary means, (f) adjusting said count of said timing pulses in response to detecting said indexing means to produce drive pulses at an increased repetition rate and thereby increase said speed of said stepping motor means for a predetermined skip period upon detection of said indexing means, and (g) resetting said count after said skip period to operate said stepping motor means at said speed corresponding to said predetermined pumping rate for a predetermined pumping period and until next detection of said indexing means.

5. The method claimed in claim 4, including controlling the lengths of said skip and pumping periods by counting said drive pulses.

* * * * *